United States Patent [19]

Bergmann

[11] Patent Number: 5,168,041

[45] Date of Patent: Dec. 1, 1992

[54] METHOD FOR THE DETERMINATION OF OSTEOCALCIN IN HUMAN SERUM OR PLASMA

[75] Inventor: Andreas E. Bergmann, Berlin, Fed. Rep. of Germany

[73] Assignee: Henning Berlin GmbH Chemie-und Pharmawerk, Berlin, Fed. Rep. of Germany

[21] Appl. No.: 416,728

[22] Filed: Oct. 3, 1989

[30] Foreign Application Priority Data

Oct. 5, 1988 [DE] Fed. Rep. of Germany ....... 3833936

[51] Int. Cl.$^5$ .................... G01N 33/53; C12Q 1/37; C12N 9/96

[52] U.S. Cl. ...................................... 435/7.1; 435/23; 435/24; 435/188; 435/962; 435/963; 435/968; 436/536; 436/538; 436/542; 436/804; 436/811; 436/825

[58] Field of Search ............... 435/7.1, 188, 962, 963, 435/968, 23, 24; 436/536, 538, 542, 804, 811, 825

[56] References Cited

U.S. PATENT DOCUMENTS

| | | | |
|---|---|---|---|
| 4,082,612 | 4/1978 | Robbins et al. | 436/216 X |
| 4,438,208 | 3/1984 | Daftos et al. | 436/545 X |
| 4,505,853 | 3/1985 | Goldstein et al. | 530/330 X |
| 4,981,952 | 1/1991 | Yan | 530/413 X |

OTHER PUBLICATIONS

Wilkinson in *The Principles and Practice of Diagnostic Enzymology*, Edward Arnold Pub.: Chicago (1976), pp. 156–158.

Wilkes et al., *J. Biol. Chem.*, 260:13154, 1985.

Hohmann, A. et al., *J. Immunol. Methods*, vol. 64 (1983) 199–204.

Eskay, R. L. et al., *Endocrinology*, vol. 98, (1976) 269–277.

Primary Examiner—Esther L. Kepplinger
Assistant Examiner—Toni R. Scheiner
Attorney, Agent, or Firm—Cushman, Darby & Cushman

[57] ABSTRACT

A method is known for the determination of osteocalcin in human serum or plasma, in which a sample of the biological fluid containing the osteocalcin to be determined is incubated, together with a defined amount of an oligopeptide tracer, with a suitable anitbody which binds both the osteocalcin and the tracer. This method has proved to be susceptible to error in that the incubation conditions affected the measured levels, and the osteocalcin levels obtained were often too high. The recognition that the observed errors are attributable to a proteolytic breakdown of the oligopeptide tracer by constituents of the serum or plasma resulted in the technical teaching of the addition of one or more proteolysis inhibitors to the sample of human serum or plasma before or together with the addition of the oligopeptide tracer, specifically either a mixture of an endopeptidase inhibitor with an aminopeptidase inhibitor or, when an N-terminally protected oligopeptide tracer is used, only an endopeptidase inhibitor. Preferred inhibitors are amastatin and leupeptin.

9 Claims, No Drawings

METHOD FOR THE DETERMINATION OF OSTEOCALCIN IN HUMAN SERUM OR PLASMA

The present invention relates to a method for the determination of osteocalcin in human serum or plasma. The method is an immunoassay in which a sample of the serum or plasma containing the h-osteocalcin to be determined is incubated, together with a defined amount of an oligopeptide tracer which is defined in detail hereinafter and which contains a labelling group detectable with suitable physical detection methods, with an antibody which represents a specific binder for the osteocalcin and the oligopeptide tracer, after which the proportion of the oligopeptide tracer bound to the antibody is measured on the basis of its labelling and, from this, the amount of h-osteocalcin contained in the serum or plasma is determined by calculation.

Human osteocalcin, which is also called vitamin K-dependent bone protein or γ-carboxyglutamic acid-containing protein (also bone Gla protein (BGP)), is a specific peptide constituent of the bone matrix. The peptide consists of 49 amino acids and has the following amino acid sequence:

Tyr—Leu—Tyr—Gln—Trp—Leu—Gly—Ala—Pro—Val—Pro—Tyr—Pro—Asp—
Pro—Leu—Glu—Pro—Arg—Arg—Gla—Val—Cys—Gla—Leu—Asn—Pro—Asp—
Cys—Asp—Glu—Leu—Ala—Asp—Arg—Ile—Gly—Phe—Gln—Glu—Ala—Tyr—
Arg—Arg—Phe—Tyr—Gly—Pro—Val$^{49}$

The peptide is synthesized by the osteoblasts, and a small fraction of the osteocalcin which is formed is released into the blood. Determination of the concentration of this osteocalcin in the blood makes it possible to draw certain valuable conclusions about the metabolism of bone, reference being made, for supplementary information, to the paper by Lian, J. B. and Gundberg, C. M. in: Clinical Orthopaedics and Related Research, 226, pages 267 to 291 (1988). According to this, determination of the osteocalcin concentration in human serum or plasma makes it possible to obtain information which may be of assistance for the diagnosis and therapy of disturbances of bone metabolism.

Various immunodiagnostic methods, in particular radioimmunoassays, have been developed for measuring the osteocalcin concentration. The present invention relates to an inventive further development, which is important for its practical applicability, of an immunodiagnostic detection method which is based on the teaching of U.S. Pat. No. 4,438,208. According to the said US patent, various oligopeptides which represent fragments of intact h-osteocalcin, in particular the C-terminal tridecapeptide of h-osteocalcin (h-osteocalcin 37-49), are used to raise antibodies which are directed against this peptide segment of human osteocalcin and are then employed for a radioimmunoassay for the determination of intact h-osteocalcin 1-49. Used as tracer in the immunoassay, which operates on the known competition principle, is an oligopeptide tracer which represents a labelled osteocalcin 37-49 or preferably represents as osteocalcin 38-49 analogue tracer an oligopeptide with the following structure.

Tyr$^{38}$-Gln-Glu-Ala-Phe-Arg-Arg-Phe-Phe-Gly-Pro-Val$^{49}$

The binding of this analogue tracer to the anti-osteocalcin 37-49 antibody decreases with increasing concentration of osteocalcin 1-49 in the investigated sample. The amount of osteocalcin 1-49 present in the sample (incubation mixture) can therefore be quantified in a customary manner using an osteocalcin 37-49 standard plot. It is assumed in U.S. Pat. No. 4,438,208 that an assay of this type will be suitable for the determination of human osteocalcin in, for example, human serum.

Compared with an immunoassay which operates by use of antibodies against the complete osteocalcin or by use of osteocalcin 1-49 tracers, the method of U.S. Pat. No. 4,438,208 has many important advantages: the antibody is directed against an amino acid sequence which corresponds to a defined region of human osteocalcin, namely its C-terminal part. There is no calcium binding site in this part and, consequently, the osteocalcin 1-49-/antibody interaction is independent of the calcium concentration.

Furthermore, the abovementioned 38-49 analogue tracer can be used. The latter is an analogue peptide which contains only one tyrosine unit. This means that the tracer can easily be obtained in pure form (for example by HPLC) after a radioiodination (for example using the known chloramine T method). Osteocalcin 1-49 contains 5 tyrosine units, and even the osteocalcin 37-49 oligopeptide still contains 2 tyrosine units. Radiodination of these peptides usually results in several differently labelled products which must be separated for use as tracer, which causes problems.

However, it has been established in attempts to determine osteocalcin in human serum (or plasma) that the measured levels differed depending on the incubation conditions and that the apparent osteocalcin levels in the sample to be assayed were often too high.

The present invention has the object of designing a method for determination of h-osteocalcin, in which a sample of a biological fluid containing the osteocalcin to be determined is incubated, together with a defined amount of an oligopeptide tracer, in particular of an osteocalcin 38-49 analogue tracer, which contains a labelling group detectable with suitable detection methods, with an antibody which represents a specific binder for the osteocalcin and the oligopeptide tracer, after which the proportion of the oligopeptide tracer bound to the antibody is measured on the basis of its labelling and, from this, the amount of osteocalcin contained in the serum or plasma is determined by calculation, in such a way that a reliable and reproducible determination of h-osteocalcin in a human serum or plasma is made possible.

This object is achieved in a method according to the precharacterizing clause of patent claim 1 by the measure described in the characterizing clause.

Preferred advantageous embodiments of the basic method according to patent claim 1 are described in the subclaims.

The basis for the method according to the invention is the recognition by the inventor that the incorrect measured results and the too high levels of osteocalcin measured in samples of human serum or plasma derive from the fact that the latter contain proteases which rapidly degrade the analogue tracer during the incubation of tracer, antibody and sample. The fragments of the analogue tracer formed by this are no longer bound by the antibody so that, by reason of the reduced amounts of tracer bound to the antibody, the apparent osteocalcin levels in the sample to be assayed are incorrect, namely too high It was also established at the same time that the osteocalcin 37-49 oligopeptide is also broken down in samples of human serum or plasma at a rate similar to that of the analogue tracer. The results of these investigations explained the observed incorrect measured results and allowed the conclusion to be drawn that it is not possible reliably to determine osteocalcin directly in human serum or plasma using the method of U.S. Pat. No. 4,438,208.

However, once it had been recognized that the problem is the proteolytic breakdown of the oligopeptide tracer used, it was possible to develop strategies for solving this problem, and these then finally resulted in the production of the method according to the invention. If the proteolytic breakdown of the oligopeptide tracer represents the problem to be solved, it appeared worthwhile to attempt to reduce the activity of the proteases breaking down the tracer, at least for the duration of the incubation of the tracer, antibody and serum/plasma, to an extent such that the tracer remains stable.

Various measures appeared possible for reducing the protease activities: thus, it was possible to conceive separating the proteases from the osteocalcin to be measured, for example by extraction of the osteocalcin from the serum or plasma sample. However, the extraction of patients' sera/plasmas is an elaborate method which is time-consuming and costly and therefore appears little suited to practical use.

Another conceivable method was thermal denaturation and thus inactivation of the proteases. However, heat-treatment of sera/plasmas is possible only up to a temperature of 58° C., because constituents in the serum/plasma flocculate out at higher temperatures which in turn may have negative consequences for the accuracy of an osteocalcin radioimmunoassay. However, in this connection, it emerged that sera treated at 58° C. for 1 h showed no essential changes with regard to the activity of the observed osteocalcin 38–49 (analogue tracer) breakdown. Thus, the maximum temperature of 58° C. possible for heat treatment of sera is insufficient to inactivate the proteases contained in the samples.

Another possible measure which could be considered was inhibition of the proteases by addition of suitable inhibitors. Since it was not known which proteases are present in human serum and plasma and are active with regard to the fragmentation of osteocalcin 38–49 (analogue tracer), it was not possible to predict whether a measure of this type for inhibiting the proteases with suitable inhibitors is possible and, if it is, which inhibitors would then be effective for achieving the desired object.

It emerged from extensive investigations, which are summarized in table 1, that it was not possible to suppress the breakdown of unchanged osteocalcin 38–49 (analogue tracer) by addition of a single protease inhibitor. When it was concluded from this that human serum or plasma contains more than one protease breaking down the oligopeptide tracer, and when thereafter mixtures of protease inhibitors were investigated, a way of achieving the object on which the invention is based became evident.

This is because it was established that a mixture of leupeptin and amastatin, neither of which alone sufficiently suppressed the breakdown of the oligopeptide, prevents the breakdown of the oligopeptide tracer.

This result is also evident from table 1 which follows.

TABLE 1

Effect of various protease inhibitors on the hydrolysis of $^{125}$I-osteocalcin 38–49 (analogue tracer).

| Inhibitor | Concentration | % of the hydrolysis rate of the control |
|---|---|---|
| Control | / | 100 |
| Ethylenediaminetetra-acetate | 10 mM | 100 |
| Diisopropyl fluorophosphate | 1 mM | 100 |
| Phenylmethylsulfonyl fluoride | 2 mM | 100 |
| p-Chloromercuriphenyl-sulphonic acid | 1 mM | 100 |
| N-Ethylmaleimide | 2 mM | 100 |
| Bestatin | 1 mM | 100 |
| Amastatin | 100 μM | 88 |
| Pepstatin | 100 μM | 100 |
| Elastatinal | 100 μM | 100 |
| Leupeptin | 1 mM | 100 |
| Phosphoramidon | 1 mM | 100 |
| Benzamidine | 1 mM | 100 |
| Trasylol | 1.6 × 10$^6$ units/ml | 100 |
| Heparin | 5 mg/ml | 100 |
| Trypsin inhibitor (soybean) | 0.1 mg/ml | 100 |
| Antithrombin III | 0.1 units/ml | 100 |
| Heat treatment (1 h/58° C.) | / | 100 |
| Leupeptin Amastatin | 1 mM – 100 μM | <2 |

In this connection, the investigation of the proteolysis of the osteocalcin 38–49 (analogue tracer) labelled with $^{125}$I was conducted as described in detail in the examples hereinafter.

The surprising effectiveness of the combination of leupeptin and amastatin with regard to the fragmentation of osteocalcin 38–49 (analogue peptide) as well as of—as emerged from subsequent investigations—osteocalcin 38–49 in the same biological fluids then allowed the conclusion to be drawn, by reason of the known inhibitory actions of leupeptin and amastatin, that the fragmentation of the oligopeptide tracer is brought about both by one (or various) endopeptidase(s) (leupeptin is an endopeptidase inhibitor) and by one (or various) aminopeptidase(s) (amastatin is an aminopeptidase inhibitor).

Since aminopeptidases are known to cleave peptides only when the amino group of the N-terminal amino acid is present in free form, it was possible to find another variant for achieving the object according to the invention: it is possible by blocking the free amino group (for example by acetylation) to protect the oligopeptide from breakdown by the aminopeptidases. Thus, if an oligopeptide with a protected amino group at the N-terminus and, at the same time, an inhibitor of endopeptidases (for example leupeptin) are employed, it is likewise possible to prevent the breakdown of the oligopeptide tracer employed in protected form.

While the protected oligopeptide continues to be rapidly fragmented in serum/plasma, in this case it suffices to add leupeptin alone in order completely to suppress this breakdown. Table 2 which follows summarizes these results. According to this ($^{125}$I)-N-acetyl-osteocalcin (38-49)(analogue peptide) is rapidly fragmented in serum/plasma. However, addition of leupeptin in the minimum concentration required suppresses this breakdown.

TABLE 2

Effect of leupeptin on the breakdown of $^{125}$I-N-acetylosteocalcin 38-49 (analogue peptide).

| Inhibitor | Concentration | % of the hydrolysis rate of the control |
|---|---|---|
| Control | / | 100 |
| Leupeptin | 50 μM | 0 |

The breakdown was followed as described in detail in the examples.

The object according to the invention is thus achieved by carrying out the determination of osteocalcin in a sample of human serum or plasma in the presence of one or more proteolysis inhibitors preventing the proteolytic breakdown of the oligopeptide tracer.

If an unprotected oligopeptide tracer, for example the preferred osteocalcin 38-49 (analogue peptide) oligopeptide tracer, is used, it is necessary to use suitable proteolysis inhibitors against the endopeptidase present in human serum or plasma as well as the aminopeptidase. In this connection, these proteolysis inhibitors must be used in the relevant minimum concentration necessary for effective inhibition in the incubation mixture.

In the case of the preferred endopeptidase inhibitor leupeptin, this minimum concentration is 50 μM, and in the case of the preferred aminopeptidase inhibitor amastatin, this minimum concentration is 25 μM.

The said proteolysis inhibitors leupeptin and amastatin are known substances and are also commercially available. Amastatin is described, for example, in the article "Inhibitors of metalloproteases" by James C. Power and J. Wade Harper in "Proteinase Inhibitors", edited by Barrett and Salvesen, 1986 Elsevier Science Publishers BV (Biomedical Division). Leupeptin is likewise a known protease inhibitor and is mentioned, for example, in the "Inhibitor peptides" entry in the "Concise Encyclopedia of Biochemistry", de Gruyter, 1983.

The method according to the invention is preferably carried out as a radioimmunoassay (RIA) in which case the oligopeptide tracer is radioactively labelled with $^{125}$I. However, in place of the said radioactive labelling, it is also possible to use any other labelling used in the area of immunodiagnostics, for example other radionuclides, enzymes, fluorescent radicals, chemiluminescent radicals, magnetic particles, stable free radicals etc.

The antibody employed in the method according to the invention can be both a polyclonal and a monoclonal antibody.

This antibody can be present in dissolved or dispersed form, but is preferably immobilized by binding to a suitable solid phase, which facilitates the separation of bound and free phases. The known double antibody technique is preferably used when working in a homogeneous phase.

The possibility, which is provided by the method according to the invention, of direct determination of osteocalcin in human serum or plasma is an important prerequisite for routine osteocalcin determination in clinical practice.

The determinations resulting in the production of the present invention are explained in more detail hereinafter.

$^{125}$I-Osteocalcin 38-49 (analogue tracer)

The analogue tracer was prepared by radioiodination by the known chloramine T method using osteocalcin 38-49 which is obtainable as a commercial product (Bachem).

$^{125}$-N-Acetyl-osteocalcin 38-49 analogue tracer

Firstly, osteocalcin 38-49 (analogue peptide) was reacted with acetic anhydride to prepare the N-terminally protected N-acetyl-osteocalcin 38-49 analogue peptide. The latter was then, after purification by means of reverse phase high-pressure liquid chromatography (RPLC), radioiodinated by the known chloramine T method. The radioiodinated product was in turn purified by RPLC.

Investigation of the Inhibition of the Proteolytic Fragmentation of Osteocalcin Oligopeptides and Analogue Peptides $^{125}$I-Osteocalcin 38-49 analogue peptide, N-acetyl-$^{125}$I-osteocalcin 38-49 analogue peptide and $^{125}$I-osteocalcin 37-49 were each mixed in amounts of $2 \times 10^6$ cpm in 5 μl of water with 40 μl of buffer (25 mM sodium phosphate, 3 mM EDTA, 0.1% NaN$_3$, pH 7.8). Pure buffer was used for the control measurement, and for investigation of the various proteolysis inhibitors the latter were added, in concentrations resulting in the concentrations specified in Table 1 or 2 in the incubation mixture, with the buffer. 5 μl of human serum or plasma were then added, and this was followed by incubation at 37° C. for 10 minutes. The reaction was then stopped by addition of 100 μl of HCl (0.2N). The resulting reaction mixture was investigated for the breakdown of the peptide. The analysis of the particular peptide employed and its breakdown products was carried out by HPLC using a μBondapak C$_{18}$ column (0.4×30 cm).

The substances were eluted using a gradient produced from a solvent A (sol A) composed of acetonitrile:water:trifluoroacetic acid in the ratio of 5:95:0.1 by volume and from a solvent B (sol B) composed of acetonitrile:water:trifluoroacetic acid in the ratio of 90:10:0.1 by volume, as follows:

Linear from 100/0 (V/V) (sol A/sol B) to 85/15 (sol A/sol B in 3 min and then linear to 50/50 sol A/sol B in 14 min. The flow rate was 1.5 ml per min. The radioactivity of the eluate was followed continuously using a radioactive monitor (Raytest). The breakdown of the radioactive peptides (in percent conversion) was determined from the resulting breakdown pattern using a computer program (Raytest).

It emerged that the peptides employed in the breakdown tests could be separated from a large number of their fragments when investigated by HPLC, so that investigation of the breakdown of the peptides is readily possible. Under the specified conditions, without addition of proteolysis inhibitors or on addition of unsuitable proteolysis inhibitors, about 80% breakdown of the employed tracer is observed after incubation with serum or plasma at 37° C. for 10 minutes.

This breakdown is more than 99% suppressed in the case of the unprotected peptide if leupeptin and amastatin are simultaneously added to the incubation mixtures in concentrations above a minimum concentration characteristic of the particular inhibitor. At the time of incubation of the peptide (tracer) with the serum or plasma these minimum concentrations of the inhibitor must be at least 50 μM for leupeptin and at least 25 μM for amastatin.

The inhibitory action of a mixture of leupeptin and amastatin was then also investigated under other incubation conditions which corresponded to the customary conditions for carrying out an osteocalcin radioimmunoassay. Even on incubation of this type at 4° C. for 20 hours no breakdown of the tracer was observed in the presence of the mixture of the said proteolysis inhibitors.

Table 1 summarizes the results for the incubation at 37° C. The proteolysis inhibitors employed were obtained commercially from the suppliers specified in parentheses hereinafter: amastatin (NovaBiochem); leupeptin (Bachem); bestatin (Bachem); elastatinal (Sigma); pepstatin (NovaBiochem); phosphoramidon (NovaBiochem); benzamidine (Sigma); Trasylol (Bayer); trypsin inhibitor from soybean (Sigma); antithrombin III (Sigma).

Breakdown Tests on the N-acetyl-$^{125}$I-Osteocalcin 38–49 Analogue Peptide

On incubation with human serum or plasma under the above conditions at 37° C. for 10 minutes about 70% of the acetylated analogue peptide employed are broken down.

If leupeptin (minimum concentration 50 μM) is added to the incubation mixtures this breakdown is completely suppressed.

As in the case of the unprotected peptides, the presence of leupeptin completely prevents the breakdown of the protected analogue tracer even under the conditions for carrying out an osteocalcin radioimmunoassay.

These results are summarized in table 2.

Radioimmunoassays

It was established that the binding plots for N-acetyl-$^{125}$I-osteocalcin 38–49 analogue peptide (for the protected analogue tracer) when it is used in an osteocalcin radioimmunoassay are very similar to those of the unprotected osteocalcin 38–49 analogue peptide, so that the acetylated analogue tracer can also be used as oligopeptide tracer in a radioimmunoassay of this type.

It was established that although addition of amastatin and leupeptin reliably prevented the proteolytic breakdown of tracer, it had no other noteworthy effect on the osteocalcin radioimunoassay.

All the radioimunoassay investigations were carried out using the "OSCAtest - Osteocalcin (37–49) human (Bone Gla Protein, BGP)" supplied by Henning Berlin GmbH in accordance with the instructions specified for this radioimmunoassay.

I claim:

1. A method for the determination of osteocalcin in human serum or plasma comprising:
   (a) incubating a sample of said human serum or plasma containing osteocalcin with
      (i) a defined amount of an oligopeptide tracer comprising a sequence of 10 to 16 amino acids corresponding to the sequence of the C-terminal amino acids of human osteocalcin, wherein up to three amino acids of said sequence may be replaced by other amino acids, with the proviso that a maximum of one amino acid replacement is not a Phe/Tyr replacement or a Glu/Gla replacement, and which contains a labelling group detectable by suitable detection methods;
      (ii) an antibody which is a specific binder for the osteocalcin and the oligopeptide tracer; and
      (iii) leupeptin, as an endopeptidase inhibitor, and amastatin, as an aminopeptidase inhibitor, both inhibitors being present in amounts effective for preventing the proteolytic breakdown of said oligopeptide tracer; and
   (b) measuring the proportion of oligopeptide tracer bound to the antibody on the basis of said labelling group; and
   (c) determining by calculation the amount of osteocalcin in said human serum or plasma.

2. A method according to claim 1, wherein a minimum concentration of amastatin of 25 μM and a minimum concentration of leupeptin of 50 μM are provided in the incubation mixture which contains the sample, the oligopeptide tracer and the antibody.

3. A method according to claim 1 wherein the oligopeptide tracer is an oligopeptide of the following sequence of amino acids

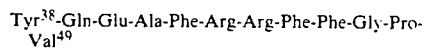

which is labelled with radioactive iodine in the Tyr residue.

4. A method according to claim 1, wherein said oligopeptide tracer is introduced into the incubation mixture in a buffer solution diluent which contains EDTA.

5. A method for determination of osteocalcin in human serum or plasma comprising:
   (a) incubating a sample of human serum or plasma containing osteocalcin with
      (i) a defined amount of an oligopeptide tracer which comprises a sequence of 10 to 16 amino acids corresponding to the sequence of C-terminal amino acids of human osteocalcin, wherein up to three amino acids of said sequence may be replaced by other amino acids, with the proviso that a maximum of one amino acid replacement is not a Phe/Tyr replacement or a Glu/Gla replacement, wherein the oligopeptide tracer has been protected through the addition of a protective group for the amino group of its N-terminal amino acid, and which oligopeptide tracer contains a labelling group detectable by suitable detection methods;
      (ii) an antibody which is a specific binder for the osteocalcin and the oligopeptide tracer; and
      (iii) leupeptin, an endopeptidase inhibitor, in an amount sufficient to prevent the proteolytic breakdown of said protected oligopeptide tracer;
   (b) measuring the proportion of oligopeptide tracer bound to the antibody on the basis of said labelling group; and
   (c) determining by calculation the amount of osteocalcin in said human serum or plasma.

6. A method according to claim 5, wherein the oligopeptide tracer is in oligopeptide of the following sequence of amino acids:

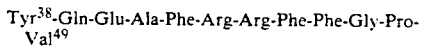

which oligopeptide is labelled with radioactive iodine in the Tyr residue and wherein the N-terminal amino acid of the oligopeptide is protected.

7. A method according to claim 5, wherein said oligopeptide tracer is introduced into the incubation mixture in a buffer solution diluent containing EDTA.

8. A method according to claim 5 or 6, wherein the oligopeptide tracer is protected by acetylation of the N-terminal amino acid.

9. A method according to claim 5, wherein leupeptin is added in such an amount that its concentration in the incubation mixture containing the sample, the oligopeptide tracer and the antibody is at least 50 μM.

* * * * *